United States Patent
Gervay-Hague et al.

(10) Patent No.: US 9,586,984 B2
(45) Date of Patent: Mar. 7, 2017

(54) ONE-POT SYNTHESIS OF ALPHA/BETA-O-GLYCOLIPIDS

(71) Applicant: The Regents of the University of California, Oakland, CA (US)

(72) Inventors: Jacquelyn Gervay-Hague, Davis, CA (US); Wenjun Du, Mount Pleasant, MI (US); Suvarn S. Kulkarni, Mumbai (IN); Matthew Schombs, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 44 days.

(21) Appl. No.: 14/148,477

(22) Filed: Jan. 6, 2014

(65) Prior Publication Data

US 2014/0221633 A1 Aug. 7, 2014

Related U.S. Application Data

(62) Division of application No. 12/595,214, filed as application No. PCT/US2008/059666 on Apr. 8, 2008, now Pat. No. 8,624,006.

(60) Provisional application No. 60/910,728, filed on Apr. 9, 2007.

(51) Int. Cl.
| | |
|---|---|
| *C07H 15/10* | (2006.01) |
| *C07H 1/00* | (2006.01) |
| *C07H 5/00* | (2006.01) |
| *C07H 5/06* | (2006.01) |
| *C07H 15/04* | (2006.01) |
| *C07H 15/06* | (2006.01) |
| *C07J 17/00* | (2006.01) |

(52) U.S. Cl.
CPC .............. *C07H 1/00* (2013.01); *C07H 5/00* (2013.01); *C07H 5/06* (2013.01); *C07H 15/04* (2013.01); *C07H 15/06* (2013.01); *C07H 15/10* (2013.01); *C07J 17/005* (2013.01)

(58) Field of Classification Search
None
See application file for complete search history.

(56) References Cited

U.S. PATENT DOCUMENTS

| | | | |
|---|---|---|---|
| 4,751,290 A * | 6/1988 | Ogawa | ............... C07H 15/10 536/123 |
| 5,116,821 A | 5/1992 | Randall et al. | |
| 5,936,076 A | 8/1999 | Higa et al. | |
| 6,017,426 A | 1/2000 | Semeria et al. | |
| 6,143,724 A | 11/2000 | Ohira et al. | |
| 6,645,935 B2 | 11/2003 | Danishefsky et al. | |
| 7,067,698 B2 | 6/2006 | Wender et al. | |
| 2006/0019246 A1 | 1/2006 | Tsuji et al. | |

OTHER PUBLICATIONS

Chida et al., "Total Synthesis of Acanthacerebroside A and Astrocerebroside A via a Chiral Epoxide Intermediate Derived from L-Quebrachitol" Bull Chem Soc Jpn (1998) vol. 71 pp. 259-272.*
Peterson et al., "N-Diphenylmethylene-Protected Glycosyl Acceptors. Selective 8-0-Glycosylation to Form Lactosyl-tlireo-Ceramide" Journal of Organic Chemistry (1993) vol. 58 pp. 4309-4314.*
Murakami et al., "Efficient stereocontrolled synthesis of sphingadienine derivatives" (Tetrahedron (2005) vol. 61 pp. 9233-9241.*
Ito et al., "A Novel Strategy for Synthesis of Ganglioside GM3 Using an Enzymatically Produced Sialoside Glycosyl Donor" J Am Chem Soc (1993) vol. 115 pp. 1603-1605.*
International Search Report and Written Opinion from PCT/US2008/059666, dated Jul. 18, 2008 (8 pages).
Du et al. "Chem. Commun." (2007) 2336-2338.
Du et al. "Organic Letters" (2005) 7, 2063-2065.
Garegg "Advances in Carbohydrate Chemistry and Biochemistry" (2004) 59, 69-134.
He et al. "Stereoselective Preparation of Ceramide and Its Skeleton Backbone Modified Analogues via Cyclic Thionocarbonate Intermediates Derived by Catalytic Asymmetric Dihydroxylation of alpha, beta-Unsaturated Ester Precursors" Journal of Organic Chemistry (2000) vol. 65 pp. 7627-7633.
Kappe et al. "Angew. Chem Int. Ed." (2004) 43, 6250-6284.
Morita et al. "Journal of Medicinal Chem." (1995) 2176-2187.
Nyholm et al. "Biochemistry" (1993) 1225-1234.

* cited by examiner

*Primary Examiner* — Eric Olson
(74) *Attorney, Agent, or Firm* — Kilpatrick Townsend & Stockton LLP

(57) ABSTRACT

The present invention provides a one-pot method of preparing an unprotected α-O-glycolipid. The first step involves contacting a protected α-iodo sugar with a catalyst and a lipid comprising a hydroxy group, under conditions sufficient to prepare a protected α-O-glycolipid. The second step involves deprotecting the protected α-O-glycolipid under conditions sufficient to prepare the unprotected α-O-glycolipid, wherein the contacting and deprotecting steps are performed in a single vessel. The present invention also provides a one-pot method of preparing an unprotected β-O-glycolipid following the steps for the preparation of the unprotected α-O-glycolipid.

4 Claims, 5 Drawing Sheets

ONE-POT SYNTHESIS OF ALPHA/BETA-O-GLYCOLIPIDS

CROSS-REFERENCES TO RELATED APPLICATIONS

This application is a divisional of U.S. application Ser. No. 12/595,214, filed Apr. 23, 2010, which is a U.S. National Stage entry under §371 of International Application No. PCT/US2008/059666, filed Apr. 8, 2008, which claims priority to U.S. Provisional Application No. 60/910,728, filed Apr. 9, 2007, and each is incorporated herein in its entirety.

STATEMENT AS TO RIGHTS TO INVENTIONS MADE UNDER FEDERALLY SPONSORED RESEARCH OR DEVELOPMENT

This invention was made with government support under Grant Nos. CHE-0210807 and OSTI 97-24412 awarded by the National Science Foundation, and Grant Nos. 5R21GM075093-02 and 1R21GM075093-01 awarded by the National Institute of Health. The government has certain rights in the invention.

BACKGROUND OF THE INVENTION

In 1993, six novel galactosyl ceramides with unique α-glycosidic linkages were isolated from the marine sponge Agelas mauritianus near Okinawa, Japan. (Natori, T. et al., Tetrahedron Lett., 34, 5591 (1993); Natori, T. et al., Tetrahedron, 50, 2771 (1994).) These compounds showed highly potent anti-tumor activities, which prompted various synthetic studies. (Motoki, K. et al., Bioorg. Med. Chem. Lett., 5, 705 (1995).) Among the many analogues synthesized, KRN7000 (see structure below) was found to be the most potent (Kobayashi, E. et al., Bio. Med. Chem., 4, 615 (1996)) and extensive mechanistic studies indicated that the anti-tumor activity was the result of CD1d-dependent natural killer T-cell (NKT) stimulation. (Kobayashi, E. et al., Bio. Med. Chem., 4, 615 (1996); Kawano, T. et al., Science, 278, 1626 (1997).) CD1d molecule is a member of the CD1 family proteins that present lipid antigens to NKT cells to activate the immune response. It is proposed that CD1d recognizes KRN7000 and the binding complex interacts with the T-cell receptor (TCR) to NKT cells stimulating the release of two major cytokines known as INF-γ and IL-4. (Wu, D. et al., Proc. Natl. Acad. Sci., 102, 1351 (2005); Porcelli, S. A. and Modlin R. L., Annu. Rev. Immunol, 17, 297 (1999); Kinjo, Y. et al., Nature, 434, 520 (2005).) The two cytokines, however, can cancel each other's beneficial therapeutic effect as one pathway down-regulates the other. (Pal, E. et al., J. Immunol., 166, 662 (2001); Berkers, C. R. and Ovaa, H., Trends. Pharmacol. Sci., 26, 252 (2005).) Interestingly, different KRN7000 analogs selectively stimulate cytokine production. For example, OCH (see structure below), which has only 9 carbons in the acyl chain of ceramide, produces predominately IL-4 and exhibits greater efficacy than KRN7000 against the autoimmune disease experimental allergic encephalomyelitis. (Pal, E. et al., J. Immunol., 166, 662 (2001); Miyamoto, K. et al., Nature, 413, 531 (2001).) Whereas, the C-glycoside analogue of KRN7000, cKRN7000 (see structure below) upregulates IFN-γ and is 100 times more potent than KRN7000 in inhibiting tumor growth in mice. (Yang, G. et al., Angew. Chem. Int. Ed, 43, 3818 (2004).)

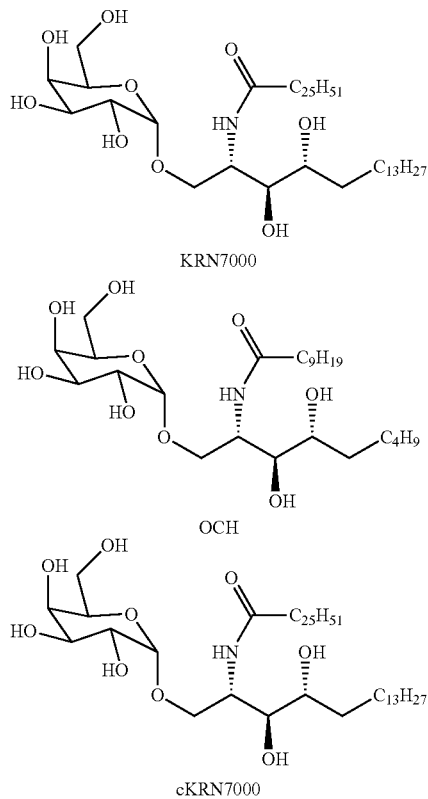

Numerous efforts have been invested in the syntheses of α-GalCer analogs to access these biologically important compounds in pure form for biological and biomedical studies. However, considerable challenges remain. Arguably, the biggest hurdle in the synthesis is the glycosylation reaction, which often gives low yields and poor α/β selectivity. To achieve the desired chemo- and stereoselectivity, multi-step protections and deprotections are required lowering the overall synthetic efficiency. Initially, glycosyl fluorides (Sakai, T. et al., J. Med. Chem., 41, 650 (1998); Ndonye, R. M. et al., J. Org. Chem., 70, 10260 (2005); Kim, S. et al., Synthesis, 847 (2004); Morita, M. et al., J. Med. Chem., 38, 2176 (1995)) and trichloroacetimidates (Kim, S. et al., Synthesis, 847 (2004); Xia, C. et al., Bioorg. Med. Chem. Lett., 16, 2195 (2006); Plettenburg, O. et al., J. Org. Chem., 67, 4559 (2002); Figueroa-Perez, S, and Schmidt, R. R., Carbohydrate Research, 328, 95 (2000)) were the most commonly used glycosyl donors. These protocols gave marginal yields (30%-60%) and were often complicated by the formation of α/β mixtures. Other glycosyl donors such as bromides (Goff, R. D. et al., J. Am. Chem. Soc., 126, 13602 (2004), thiogalactoside (Plettenburg, O. et al., J. Org. Chem., 67, 4559 (2002)), and phosphites (Luo, S. Y. et al., J. Org. Chem., 71, 1226 (2006)) have also been employed, however neither yields nor stereoselectivities were improved.

Recently, a significant advance in the glycosylation reaction using glycosyl iodide donors was reported. (Du, W. and Gervay-Hague, J., Org. Lett., 7, 2063 (2005).) Reactions of per-O-benzylated galactosyl iodide with an azido sphingosine in the presence of tetrabutylammonium iodide afforded exclusively the α-anomer in over 90% yield. An azido group is used in place of the amide because, if left intact during the glycosylation, the amide deactivates the primary hydroxyl of the acceptor through unfavorable hydrogen bonding interactions. (Polt, R. et al., *J. Am. Chem. Soc.,* 114, 10249 (1992); Schmidt, R. R. and Zimmermann, P., *Angew. Chem. Int. Ed.,* 25, 725 (1986).)

There have been several attempts to incorporate fully functionalized glycolipids as acceptors but with limited success. Ceramide acceptors as such give complex mixtures with per-O-benzylated fluoride and trichloroacetimidate donors; whereas a TBS-protected ceramide acceptor affords coupling products in moderate yields and selectivity (e.g., Fluoride, 68%, α/β=1.7/1; imidate, 63%, only α). (Kim, S. et al., *Synthesis,* 847 (2004).) Similarly, 3,4,6-tri-O-acetyl, 2-O-benzyl galactosyl bromide had been coupled with acetylated acceptor in 62% yields to obtain α-linked product along with a minor, difficult to separate, β-isomer. (Goff, R. D. et al., *J. Am. Chem. Soc.,* 126, 13602 (2004).)

As discussed above, a major challenge in the synthetic pathway of glycolipids is the glycosylation reaction, which often gives low yields and poor α/β selectivity. Historically, the most common method to synthesize β-linked glycolipids involved the glycosylation between a protected lipid acceptor (usually azido-sphingosine or azido-phytosphingosine) and a protected donor containing a C2 participating group designed to capitalize on anchiomeric assistance. Some common examples from the literature include the use of per-O-benzoylated thiogalactosides (Fukunaga, K. et al., *Bioorg. Med. Chem. Lett.,* 13, 813, (2003)), per-O-acetyl sugars (Morita, M. et al., *Bioorg. Med. Chem. Lett.,* 5, 699, (1995)), and per-O-pivaloylated trichloroacetimidates (Matto, P. et al., *J. Org. Chem.,* 72, 7757, (2007).)

While the stereo-selectivity reported in these reactions highly favors the desired β-glycoside, the presence of a participating group at the C2 position lowers the reactivity of the donor and severely limits the options available when working towards more complex synthetic targets (such as in oligosaccharide synthesis) thereby making several (and often redundant) protection-deprotection steps required. Recently, significant advances in yield and α-selectivity of glycosylation reactions have been achieved via the use glycosyl iodide donors (Du, W., Kulkarni, S. S., Gervay-Hague, J. *Chem. Commun.,* 2336-2338 (2007)). But prior methods of making β-linked glycolipids involved multi-step schemes with isolation after each intermediate step (Lichtenthaler, F. W., Kohler, B. *Carbohydrate Research,* 258, 77-85 (1994)). What is needed is a single-pot process for preparation of α-linked and β-linked glycolipids. It is an attractive strategy to employ fully functionalized ceramide acceptors because tedious protection and deprotection steps, many subsequent to glycosidation, can be alleviated. Surprisingly, the present invention meets this and other needs.

BRIEF SUMMARY OF THE INVENTION

Figure 1:
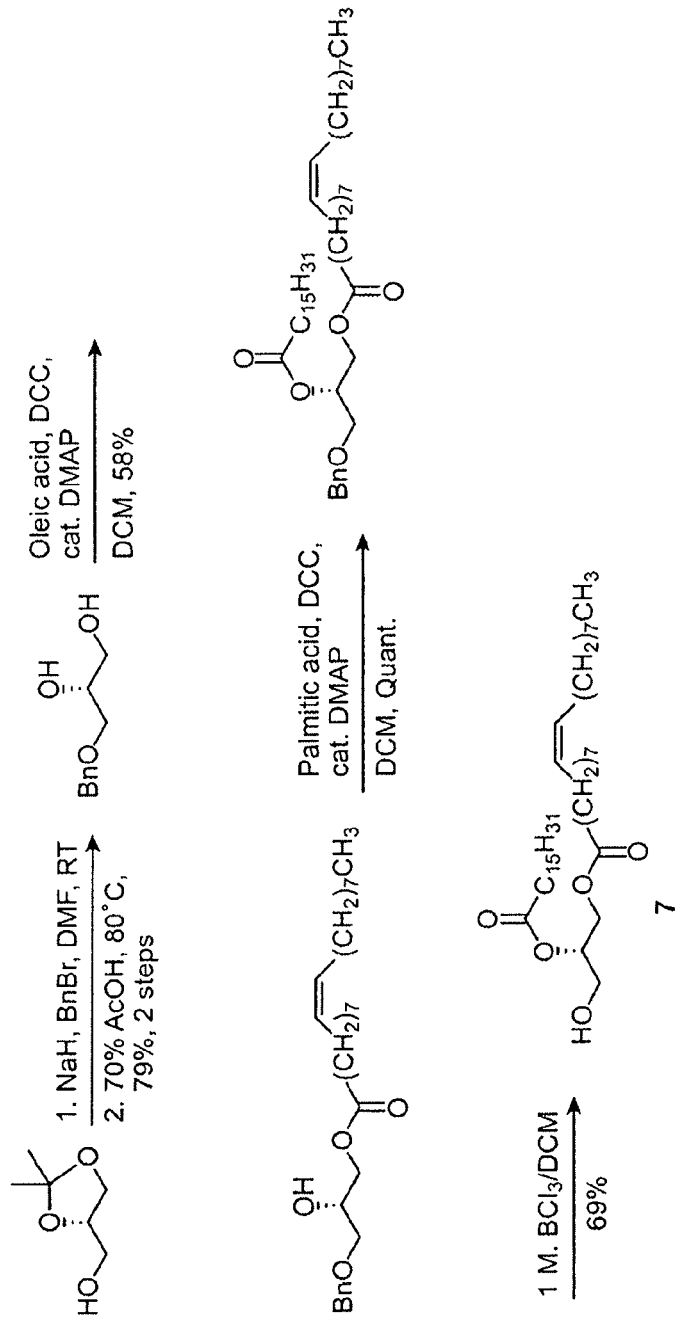
FIG. 1 shows the synthesis of lipid chain acceptor 7.

The present invention provides a one-pot synthesis of α-linked glycolipids or β-linked glycolipids. The method of the present invention prepares glycolipids in a single pot by reaction of an α-iodo sugar, such as α-iodo galactose, glucose or lactose, with a suitable catalyst and a lipid, to prepare the desired α-linked or β-linked glycolipid. The protected α-linked or β-linked glycolipid is deprotected in the same pot to afford the desired α-linked or β-linked glycolipid, without the need for separate deprotection steps.

In one embodiment, the present invention provides a method of preparing an unprotected α-O-glycolipid. One step of the method involves contacting a protected α-iodo sugar with a catalyst and a lipid having a hydroxy group, under conditions sufficient to prepare a protected α-O-glycolipid. Another step of the method involves deprotecting the protected α-O-glycolipid under conditions sufficient to prepare the unprotected α-O-glycolipid, wherein the contacting and deprotecting steps are performed in a single vessel.

In a second embodiment, the present invention provides a method of preparing an unprotected β-O-glycolipid comprising the steps of. One step of the method involves contacting a protected α-iodo sugar with a catalyst and a lipid having a hydroxy group, under conditions sufficient to prepare a protected β-O-glycolipid. Another step of the method involves deprotecting the protected β-O-glycolipid under conditions sufficient to prepare the unprotected β-O-glycolipid, wherein the contacting and deprotecting steps are performed in a single vessel.

DETAILED DESCRIPTION OF THE INVENTION

I. Introduction

The present invention provides a one-pot synthesis of α-linked glycolipids or β-linked glycolipids, depending upon the reaction conditions. Prior methods of making glycolipids use lipid derivatives that require separate protection and deprotection steps and subsequent manipulation to obtain the desired glycolipid. The method of the present invention prepares the glycolipids in a single pot by reaction of an α-iodo sugar, such as α-iodo galactose, glucose or lactose, with a suitable catalyst and a lipid, to prepare the desired α-linked or β-linked glycolipid. For α-linked glycolipids, the catalyst can be tetrabutylammonium iodide. For β-linked glycolipids, the catalyst can be silver carbonate. The protected α-linked or β-linked glycolipid is deprotected in the same pot to afford the desired α-linked or β-linked glycolipid, without the need for separate deprotection steps.

The one-pot synthesis of α-linked and β-linked glycolipids provided by the methods of the present invention makes possible the rapid and efficient synthesis of α-linked and β-linked glycolipids. As the coupling and deprotection steps can be performed in a single pot, there are significant commercial applications for the preparation of α-linked and β-linked glycolipids using the methods of the present invention.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "fatty acid" refers to a carboxylic acid having an aliphatic tail, typically from 4 to 30 carbon atoms long. Fatty acids can be saturated, mono-unsaturated or poly-unsaturated. Examples of fatty acids useful in the present invention are described below. One of skill in the art will appreciate that other fatty acids are useful in the present invention.

As used herein, the term "lipid" refers to amphiphilic compounds having a polar head group and a lipophilic hydrocarbon chain. The lipid compounds of the present invention can also have a hydroxy group. Lipids of the instant invention include, but are not limited to, glycerides such as glycerol substituted with 1 or 2 fatty acids, and ceramides. The ceramides of the present invention comprise a fatty acid in combination with a sphingosine or a phytosphingosine. One of skill in the art will appreciate that other lipids are useful in the present invention.

As used herein, the term "protected α-iodo sugar" refers to a sugar molecule having an iodo group in the alpha position of the anomeric carbon, where the hydroxy groups of the sugar are protected. Protecting groups suitable in the present invention include those described below. Sugars useful in the present include those described within. One of skill in the art will appreciate that other protected α-iodo sugar are useful in the present invention.

As used herein, the term "protected α-O-glycolipid" refers to an O-linked sugar linked to a lipid wherein the lipid is in the alpha position, and where the hydroxy groups of the sugar portion of the molecule are protected. Protecting groups suitable in the present invention include those described below. Protected α-O-glycolipids of the present invention include, but are not limited to, alpha-glycosyl-ceramides and alpha-glycosyl-glycerides. Sugars useful in the present include those described within. One of skill in the art will appreciate that other unprotected α-O-glycolipids are useful in the present invention.

As used herein, the term "β-O-glycolipid" refers to an O-linked sugar linked to a lipid wherein the lipid is in the beta position. The β-O-glycolipid can be protected or unprotected. When the β-O-glycolipid is unprotected, the hydroxy groups of the sugar portion of the molecule are unprotected. When the β-O-glycolipid is protected, the hydroxy groups of the sugar portion of the molecule are protected. Protecting groups suitable in the present invention include those described below. β-O-glycolipids of the present invention include, but are not limited to, beta-glycosyl-ceramides, beta-glycosyl-glycerides and beta-cholesteryl glycosides. Sugars useful in the present include those described within. One of skill in the art will appreciate that other β-O-glycolipids are useful in the present invention.

As used herein, the term "protecting group" refers to a compound that renders a functional group unreactive, but is also removable so as to restore the functional group to its original state. Such protecting groups are well known to one of ordinary skill in the art and include compounds that are disclosed in "Protective Groups in Organic Synthesis", 4th edition, P. G. M. Wuts and T. W. Greene, John Wiley & Sons, New York, 2007, which is incorporated herein by reference in its entirety. Protecting groups useful in the method of the present invention include, but are not limited to, trimethylsilyl, triethylsilyl, tertbutyldomethylsilyl, para-methoxybenzyl, benzyl and acetyl.

As used herein, the term "protected saccharide" refers to a monosaccharide, disaccharide, trisaccharide, oligosaccharide and polysaccharide where the hydroxy groups of the saccharide are protected. Protecting groups suitable in the present invention include those described within.

As used herein, the term "unprotected α-O-glycolipid" refers to an O-linked sugar linked to a lipid wherein the lipid is in the alpha position, and where the hydroxy groups of the sugar portion of the molecule are unprotected. Unprotected α-O-glycolipids of the present invention include, but are not limited to, alpha-glycosyl-ceramides and alpha-glycosyl-glycerides. Sugars useful in the present include those described within. One of skill in the art will appreciate that other unprotected α-O-glycolipids are useful in the present invention.

As used herein, the term "catalyst" refers to an agent that accelerates the rate of preparing the α-linked or β-linked glycolipid. Catalysts suitable in the present invention include, but are not limited to, an iodide salt, an iodine agent and a Lewis acid. In other embodiments, the catalyst is a transition metal catalyst, such as a silver catalyst. One of skill in the art will appreciate that other catalysts are useful in the present invention.

As used herein, the term "iodide salt" refers to salts of iodine. Exemplary iodide salts include, but are not limited to, sodium iodide and potassium iodide. One of skill in the art will appreciate that other iodide salts are useful in the present invention.

As used herein, the term "iodine agent" refers to a chemical agent that is capable of producing iodine or iodide. Exemplary iodine agents of the present invention include, but are not limited to, N-iodosuccinimide. One of skill in the art will appreciate that other iodine agents are useful in the present invention.

As used herein, the term "Lewis acid" refers to a chemical complex that is capable of accepting an electron pair. Examples of Lewis acids include, but are not limited to, aluminum chloride, iron(III) chloride, boron trifluoride, niobium pentachloride, trimethylsilyl triflate and ytterbium(III) triflate. One of skill in the art will appreciate that other Lewis acids are useful in the present invention.

As used herein, the term "quaternary ammonium iodide salt" refers to a salt comprising a quaternary ammonium ion and iodide. The quaternary ammonium ion can be any quaternary ammonium ion such as tetra-alkyl ammonium ion. Examples of quaternary ammonium iodide salts include, but are not limited to, tetramethyl ammonium iodide, tetrabutyl ammonium iodide and tetraoctyl ammonium iodide salt. One of skill in the art will appreciate that other quaternary ammonium iodide salts are useful in the present invention.

As used herein, the term "sugar" refers to monosaccharides, disaccharides, trisaccharides, oligosaccharides and polysaccharides.

As used herein, the term "deprotecting" refers to the removal of any protecting groups. For example, deprotecting the protected α-O-glycolipid entails removal of the protecting groups of a protected sugar. The conditions for deprotection depend on the protecting group being removed, but in all cases, the deprotection of the protected α-O-glycolipid of the present invention is performed in the same vessel as the contacting step. Protecting groups and procedures for removing them can be found in "Protective Groups in Organic Synthesis", 4th edition, P. G. M. Wuts and T. W. Greene, John Wiley & Sons, New York, 2007, which is incorporated herein by reference in its entirety.

As used herein, the term "vessel" refers to a container for performing the contacting and deprotection steps of the present invention. The vessel can be made of any suitable material, such as metal, glass, plastic and porcelain. In some instances, the vessel is suitable for use in a microwave.

III. Method of Preparing α-Linked and β-Linked Glycolipids

The present invention provides a one-pot synthesis of α-linked glycolipids and β-linked glycolipids. Prior methods of preparing glycolipids use lipid derivatives that require separate deprotection steps and subsequent manipulation to obtain the desired glycolipid. The method of the present invention prepares the glycolipids in a single pot by reaction of an α-iodo sugar, such as α-iodo galactose, glucose or lactose, with a suitable catalyst and a lipid, to prepare the desired α-linked or β-linked glycolipid. For α-linked glycolipids, the catalyst can be tetrabutylammonium iodide. For β-linked glycolipids, the catalyst can be silver carbonate. The protected α-linked or β-linked glycolipid is deprotected in the same pot to afford the desired α-linked or β-linked glycolipid, without the need for separate deprotection steps. In some embodiments, the α-linked and β-linked glycolipids of the present invention can be prepared using microwave radiation.

A. Preparation of α-Linked Glycolipids

The present invention provides a method of preparing an unprotected α-O-glycolipid. The first step involves contacting a protected α-iodo sugar with a catalyst and a lipid comprising a hydroxy group, under conditions sufficient to prepare a protected α-O-glycolipid. The second step involves deprotecting the protected α-O-glycolipid under conditions sufficient to prepare the unprotected α-O-glycolipid, wherein the contacting and deprotecting steps are performed in a single vessel.

Catalysts useful in the present invention include any catalyst suitable for linking an α-iodo sugar to a lipid. Exemplary catalysts of the present invention include, but are not limited to, an iodide salt, an iodine agent and a Lewis acid. Iodide salts can be a quaternary ammonium iodide salt, sodium iodide and potassium iodide. Quaternary ammonium iodide salts can be tetraalkyl-ammonium iodide salts such as tetramethyl ammonium iodide, tetrabutyl ammonium iodide and tetraoctyl ammonium iodide salt. In some embodiments, the quaternary ammonium iodide salt is tetra-butylammonium iodide. Other quaternary ammonium iodide salts, and other iodide salts, are useful in the method of the present invention.

Any iodine agent that accelerates the preparation of the protected α-O-glycolipid is useful in the method of the present invention. Exemplary iodine agents include N-iodosuccinimide.

Other agents can be used in the method of the present invention, such as $I_2$, ICl, IBr, AgOTf, $Ph_3PO$, DIPEA and other quaternary ammonium salts.

The present invention provides a method of preparing an unprotected α-O-glycolipid. The unprotected α-O-glycolipid can be prepared as a mixture of unprotected α-O-glycolipid and unprotected β-O-glycolipid, or as pure unprotected α-O-glycolipid. When a mixture of unprotected α-O-glycolipid and unprotected β-O-glycolipid is prepared, the unprotected α-O-glycolipid can be prepared in any ratio, such as 1:1, 2:1, 3:1, 4:1, 5:1, 6:1, 7:1, 8:1, 9:1, 10:1, 20:1, 50:1 and 100:1, among others. In some other embodiments, the unprotected α-O-glycolipid is prepared in at least a 1:1 ratio to the unprotected β-O-glycolipid. In still other embodiments, the unprotected α-O-glycolipid is prepared in at least a 10:1 ratio to the unprotected β-O-glycolipid. In a further embodiment, the unprotected α-β-glycolipid is prepared in at least a 20:1 ratio to the unprotected β-O-glycolipid. In yet another embodiment, the unprotected α-O-glycolipid is prepared in at least a 100:1 ratio to the unprotected β-O-glycolipid.

B. Preparation of β-Linked Glycolipids

The present invention provides a method of preparing an unprotected β-O-glycolipid. The first step involves contacting a protected α-iodo sugar with a catalyst and a lipid comprising a hydroxy group, under conditions sufficient to prepare a protected β-O-glycolipid. The second step involves deprotecting the protected β-O-glycolipid under conditions sufficient to prepare the unprotected β-O-glycolipid, wherein the contacting and deprotecting steps are performed in a single vessel.

Catalysts useful in the present invention include any catalyst suitable for linking an α-iodo sugar to a lipid to form a β-O-glycolipid. Exemplary catalysts of the present invention include, but are not limited to, transition metal catalysts. In some embodiments, the catalyst is a silver catalyst. In other embodiments, the catalyst can be silver halide, mercury cyanide, magnesium oxide or silver carbonate. In still other embodiments, the catalyst is silver carbonate. One of skill in the art will appreciate that other catalysts are useful in the present invention.

The present invention provides a method of preparing an unprotected β-O-glycolipid. The unprotected β-O-glycolipid can be prepared as a mixture of unprotected α-O-glycolipid and unprotected β-O-glycolipid, or as pure unprotected β-O-glycolipid. When a mixture of unprotected α-O-glycolipid and unprotected β-O-glycolipid is prepared, the unprotected β-O-glycolipid can be prepared in any ratio, such as 1:1, 2:1, 3:1, 4:1, 5:1, 6:1, 7:1, 8:1, 9:1, 10:1, 20:1, 50:1 and 100:1, among others. In some other embodiments, the unprotected β-O-glycolipid is prepared in at least a 1:1 ratio to the unprotected α-O-glycolipid. In still other embodiments, the unprotected β-O-glycolipid is prepared in at least a 10:1 ratio to the unprotected α-O-glycolipid. In a further embodiment, the unprotected β-O-glycolipid is prepared in at least a 20:1 ratio to the unprotected α-O-glycolipid. In yet another embodiment, the unprotected β-O-glycolipid is prepared in at least a 100:1 ratio to the unprotected α-O-glycolipid.

C. α-Iodo Sugars

The methods of the present invention can be performed using any protected α-iodo sugar. In some embodiments, the protected α-iodo sugar is selected from the group consisting of:

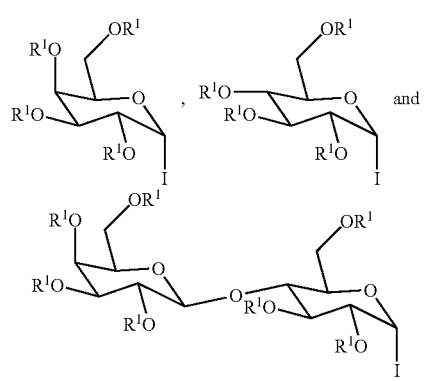

wherein each $R^1$ can be a protecting group and a protected saccharide. Any protecting group suitable for sugars and saccharides is useful in the present invention. Exemplary protecting groups include, but are not limited to, benzyl, para-methoxybenzyl (PMB), triphenylmethyl (trityl), any trialkyl silyl group, acetyl and ethers such as tetrahydropyranyl ether (THP) and methoxymethylether (MOM) groups. Trialkylsilyl protecting groups include, but are not limited to, trimethyl silyl (TMS) or triethyl silyl (TES), triisopropyl silyl (TIPS), tertbutyldimethyl silyl (TBDMS). Protecting groups are selected for their stability during subsequent transformations and for their ease of removal. Other factors may influence the choice of protecting groups. Such protecting groups are well known to one of ordinary skill in the art and include compounds that are disclosed in "Protective Groups in Organic Synthesis", 4th edition, P. G. M. Wuts and T. W. Greene, John Wiley & Sons, New York, 2007.

Any sugar is useful in the methods of the present invention, including a monosaccharide, a disaccharide, a trisaccharide, an oligosaccharide and a polysaccharide. Oligosaccharides are chains of saccharides having more than two saccharides. Polysaccharides are polymers of saccharides and can contain up to 200 or more saccharides. In some embodiments, the sugar includes, but is not limited to, galactose, glucose, lactose, galacturonic acid, glucuronic acid, L-fucose, disaccharides and trisaccharides.

In some embodiments, the protected α-iodo sugar has the structure shown below:

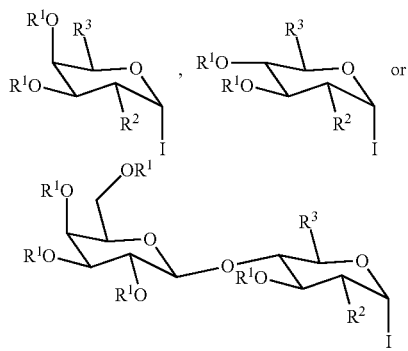

where $R^2$ can be —$OR^1$, —$N_3$ or F, and $R^3$ can be $CH_2N_3$, an aldehyde, a carboxylic acid, an ester, $CH_2$-alkyne, $CH_2$-p-$OC_6H_4C_2H_4$, $CH_2$-p-$OC_6H_4N_3$, $CH_2F$ or $CH_2OR^1$. When $R^3$ is an ester, the protected α-iodo sugar of the present invention can also have the structure shown below:

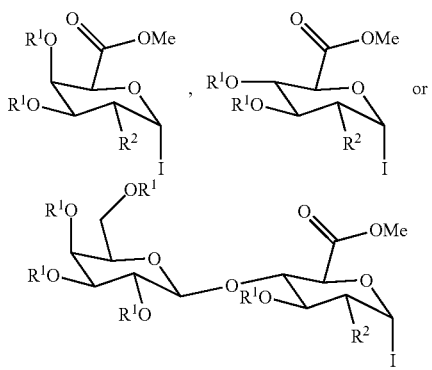

Other sugars useful as the protected α-iodo sugar of the present invention include, but are not limited to, galactose, glucuronic acid, L-fucose, and disaccharides and trisaccharides. One of skill in the art will appreciate that other sugars are useful in the present invention.

D. Lipids

Any lipid is useful in the methods of the present invention. Exemplary lipids include ceramides and substituted glycerol. When the lipid is a ceramide, the ceramide includes a fatty acid component and either a sphingosine or a phytosphingosine. In some embodiments, the lipid is a ceramide or a substituted glycerol. In other embodiments, the lipid is a ceramide. In some other embodiments, the ceramide is a sphingosine. In still other embodiments, the ceramide is a phytosphingosine. In yet other embodiments, the substituted glycerol is substituted with 1 or 2 fatty acids.

The fatty acids useful in the present invention include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). The fatty acids useful in the present invention have at least four carbon atoms in the chain. Preferably, the fatty acids of the present invention have between 10 and 26 atoms in the chain. More preferably, the fatty acids have between 14 and 22 atoms in the chain. Most preferably, the fatty acids have between 16 and 20 atoms in the chain. In other instances, it is preferred that the fatty acids of the present invention have 26 atoms in the chain. The fatty acids of the present invention can be saturated, mono-unsaturated, or poly-unsaturated. Preferably, the fatty acids are saturated. One of skill in the art will recognize that other fatty acids are useful in the present invention.

Substituted glycerol useful in the method of the present invention includes glycerol substituted with fatty acids (as described above). In some cases, the glycerol is substituted with 1 or 2 fatty acids, so that the remaining hydroxy group of glycerol can react with the α-iodo sugar.

In some embodiments, the lipid is a sphingosine derivative or phytosphingosine derivative such as:

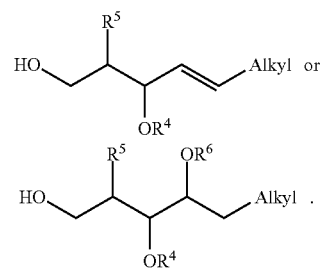

$R^4$ and $R^6$ of the formula are separately H or a protecting group, such as those described above. $R^3$ is an amine, an amide or an azide. Protecting groups useful for $R^4$ include any hydroxy protecting groups such as those listed above for $R^1$. In some embodiments, $R^4$ is a para-methoxybenzyl group. In other embodiments, $R^4$ is a tri-methyl silyl, triethyl silyl, triisopropyl silyl, or tertbutyl-dimethyl-silyl groups. In addition, $R^5$ can be an azide. Alkyl is any C1-20 alkyl, that can be branched or unbranched, saturated or partially unsaturated, and optionally substituted with hydroxy, alkoxy, aldehyde, ester or carboxy groups.

In some other embodiments, the lipid can be

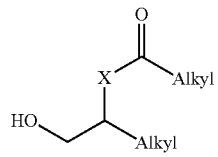

wherein X is O or NH, and alkyl is as defined above.

Conditions for preparing the unprotected glycolipids of the present invention can proceed using a variety of solvents and reagents. Solvents useful for the preparation of the unprotected glycolipids of the present invention include, but are not limited to, pyridine, triethyl amine, N-methylpyrrolidinone (NMP), dimethylformamide (DMF), methylene chloride, chloroform, benzene, toluene, acetonitrile, tetrahydrofuran (THF), ether, dioxane, glyme, diglyme, ethyl acetate, methanol, ethanol and isopropanol. In some embodiments, one solvent is used for the contacting step and a second solvent is used for the deprotecting step, following removal of the first solvent. For example, methylene chloride can be used for the first step and methanol can be used in the deprotecting step. One of skill in the art will appreciate that other solvents and solvent combinations are useful in the present invention.

The preparation of the unprotected glycolipids of the present invention can proceed at a variety of temperatures and times. Preparation of the unprotected glycolipids of the present invention can be achieved over 1-48 hours at 0-50° C. Preferably, 1-24 hours at 20-40° C. is used. In some embodiments, 2-4 hours at room temperature is used. In other embodiments, 12-48 hours at room temperature is used. One of skill in the art will appreciate that the time, temperature and solvent are dependent on each other, and changing one can require changing the others to prepare the unprotected glycolipids of the present invention.

Conditions for the deprotecting step are dependent on the type of protecting group used. For example, when the protecting group is a trialkylsilyl groupsuch as trimethylsilyl, the protected glycolipid can be deprotected using an ion exchange resin such as Dowex® 50WX8-200. Other ion exchange resins can be used for the deprotection of trialkylsilyl groupsused in the present invention. In addition, other reagents for deprotecting trialkylsilyl groups used in the method of the present invention can be used. Methods for removing deprotecting groups can be found in "Protective Groups in Organic Synthesis", 4th edition, P. G. M. Wuts and T. W. Greene, John Wiley & Sons, New York, 2007. One of skill in the art will appreciate that other conditions for removing protecting groups are useful in the present invention.

The microwave irradiation of the present invention can be performed at any appropriate time, temperature or power setting. When using microwave irradiation, the preparation of the unprotected glycolipid of the present invention can be achieved in less than 10 hours at up to 200° C. Preferably, less than 5 hours and from 50 to 150° C. The microwave can operate at a variety of power settings, up to about 1000 Watts. Preferably, the microwave operates at less than 500 Watts. One of skill in the art will appreciate that other temperatures, time and microwave power settings are useful in the present invention.

The following examples are provided by way of illustration only and not by way of limitation. Those of skill in the art will readily recognize a variety of non-critical parameters that can be changed or modified to yield essentially similar results.

IV. Examples

All reactions were conducted under a dried argon stream. Solvents ($CH_2Cl_2$ 99.8%, benzene 99.8%) were purchased in capped DriSolv™ bottles and used without further purification and stored under argon. TMSI was stored at −15° C. under desiccated atmosphere. All other solvents and reagents were purchased from commercial sources and used without further purification. All glassware utilized was flame-dried before use. Glass-backed TLC plates (Silica Gel 60 with a 254 nm fluorescent indicator) were used without further manipulation and stored over desiccant. Acceptor 6 was purchased from Avanti Polar Lipids Inc (Alabaster, Ala.). Developed TLC plates were visualized under a shortwave UV lamp, stained with an $I_2$—$SiO_2$ mixture, and/or by heating plates that were dipped in ammonium molybdate/cerium (IV) sulfate solution. Silica gel column chromatography was performed using flash silica gel (32-63 μm) and employed a solvent polarity correlated with TLC mobility. Optical rotations were measured at 598 nm on a Jasco DIP-370 digital polarimeter using a 100 mm cell. NMR experiments were conducted on a Varian 600 MHz instrument using $CDCl_3$ (99.9% D) or $CD_3OD$ (99.9%) or pyridine-$d_5$ (99.9% D) as the solvent. Chemical shifts are relative to the deuterated solvent peak and are in parts per million (ppm). Mass spectra were acquired using a Qtrap LC/MS instrument. The microwave-assisted reaction was conducted in a Discover Labmate® (CEM Co., Matthews, N.C.) microwave reactor.

TABLE 1

Results of one-pot synthesis of α-glycosides.

4

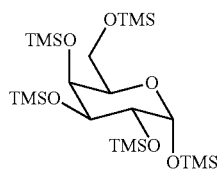

TABLE 1-continued
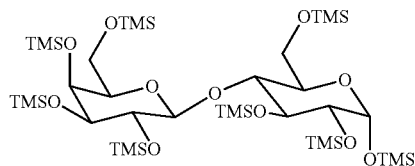
12
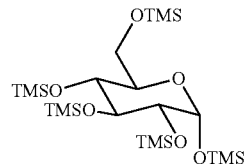
13
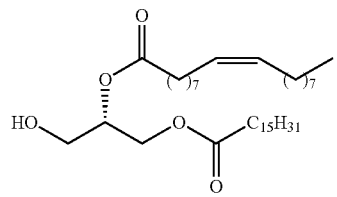
6
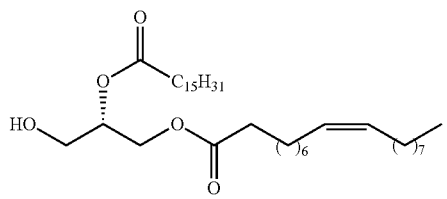
7
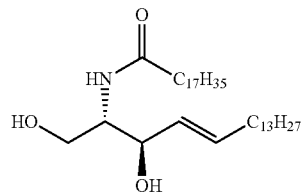
8
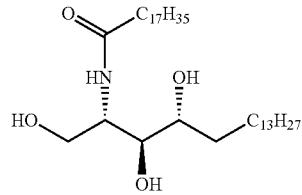
9
| Entry | Donor Precursor | Acceptor | Promoter | Product | Solvent | Conditions | α/β ratio (yield) |
|---|---|---|---|---|---|---|---|
| 1 | 4 | 6 | TBAI | 1a | Benzene | 65° C. 24 h | 10:1 (89%) |
| 2 | 4 | 6 | TBAI | 1a | CH$_2$Cl$_2$ | rt, 24 h | α only (81%) |
| 3 | 4 | 7 | TBAI | 1b | CH$_2$Cl$_2$ | rt, 36 h | α only (72%) |
| 4 | 4 | 8 | TBAI | 2 | CH$_2$Cl$_2$ | rt, 48 h | α only (77%) |
| 5 | 4 | 9 | TBAI | 3 | Benzene | 65° C. 48 h | α only (20%) |
| 6 | 4 | 9 | TBAI | 3 | CH$_2$Cl$_2$ | rt, 48 h | α only (30%) |

TABLE 1-continued

| 7 | 13 | n-octanol | TBAI | 14 | CH$_2$Cl$_2$ | rt, 48 h | α only (81%) |
| 8 | 13 | 6 | TBAI | 15 | CH$_2$Cl$_2$ | rt, 48 h | α only (58%) |
| 9 | 13 | 8 | TBAI | 16 | CH$_2$Cl$_2$ | rt, 48 h | α only (63%) |
| 10 | 12 | n-octanol | NIS | 17 | CH$_2$Cl$_2$:CH$_3$CN (1:1) | rt, 24 h | α only (58%) |

Example 1

Preparation of Compound 1a

This example provides a method for preparing compound 1a by reaction of an α-iodo galactopyranose with compound 6. Compound 1a was then hydrogenated to afford compound 1c. Compound 6 is commercially available from Avanti Polar Lipids Inc (Alabaster, Ala.).

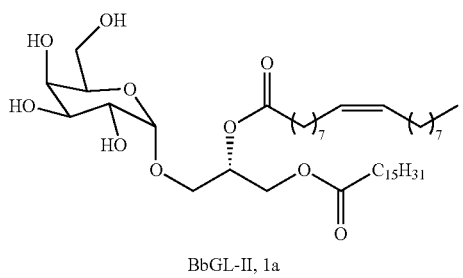

BbGL-II, 1a

1-O-Palmitoyl-2-O-oleoyl-3-O-α-D-galactopyranosyl-sn-glycerol (BbGL-II, 1a)

To a solution of 1,2,3,4,6-penta-O-trimethylsilyl-D-galactopyranose (4, 81 mg, 0.15 mmol) in CH$_2$Cl$_2$ (3 mL) at 0° C. was added TMSI (30 mg, 0.15 mmol). The reaction was stirred under argon at 0° C. for 20 min. The reaction was stopped by adding 15 mL of anhydrous benzene and solvent was evaporated under reduced pressure. The slightly yellow oil 5 was dissolved in CH$_2$Cl$_2$ (1.5 mL) and kept under argon. In a separate flask, molecular sieves (MS, 4 Å, 50 mg), TBAI (220 mg, 0.60 mmol), 6 (29 mg, 0.050 mmol) and DIPEA (58 mg, 0.45 mmol) were added into CH$_2$Cl$_2$ (1.5 mL). The mixture was stirred under argon at rt. The glycosyl iodide 5 was added dropwise and the reaction mixture was stirred at rt for 24 h. Solvent was evaporated. MeOH (15 mL) and Dowex® 50WX8-200 ion exchange resin (1 g) were added and the reaction was stirred at rt for 4 h. Resin was removed by filtration. The solvent was removed in vacuo and the resulting residue was purified by silica gel chromatography (CHCl$_3$:MeOH=10:1, R$_f$=0.36) to afford 1a as a white powder (31 mg, 81%). $[\alpha]_D^{25}$+29° (c=1.0, CHCl$_3$). $^1$H NMR (600 MHz, CDCl$_3$) δ 0.87 (t, J=6.8 Hz, 6H), 1.24-1.40 (m, 44H), 1.67 (dd, J=11.4, 7.2 Hz, 4H), 2.00 (dd, J=12.0, 6.0 Hz, 4H), 2.31 (dt, J=7.8, 5.4 Hz, 4H), 2.45 (s, 1H), 2.94 (s, 1H), 3.10 (s, 1H), 3.63 (m, dd, J=10.8, 6.0 Hz, 1H, H-3a), 3.70-3.90 (m, 6H, H-2', H-4', H-5', H6a', H6b', H-3b), 4.05-4.08 (m, 1H, H-3'), 4.13 (dd, J=6.0, 12.0 Hz, 1H, H-1b), 4.37 (dd, J=3.6, 12.0 Hz, 1H, H-1a), 4.92 (d, J=3.6 Hz, 1H, H-1'), 5.24 (dt, J=9.6, 5.4 Hz, 1H, H-2), 5.34 (dt, J=15.6, 6.8 Hz, 2H, CH═CH); $^{13}$C NMR (150 MHz, CDCl$_3$) δ 14.1, 22.67, 22.68, 24.9, 27.16, 27.21, 29.12, 29.19, 29.28, 29.31, 29.32, 29.35, 29.49, 29.52, 29.63, 29.65, 29.66, 29.69, 29.74, 31.90, 31.92, 34.1, 34.3, 62.1, 63.1, 66.6, 69.3, 69.8, 70.0, 70.2, 70.8, 99.3, 129.7, 130.0, 173.3, 173.6; ESIMS calc'd for C$_{43}$H$_{80}$NaO$_{10}$ [M+Na]$^+$ 779.56. found: 779.52.

Compound 1a was then hydrogentated to afford compound 1c.

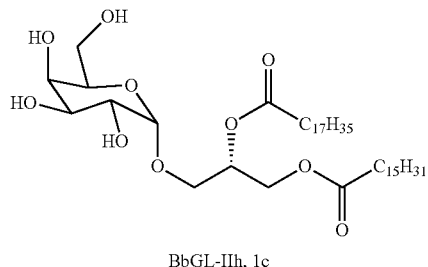

BbGL-IIh, 1c

1-O-Palmitoyl-2-O-stearoyl-3-O-α-D-galactopyranosyl-sn-glycerol (1c)

BbGl-II (1a, 26 mg, 0.034 mmol) and Pd/C (26 mg, 100% w/w) was suspended in a solution of CH$_2$Cl$_2$ (2 mL) and MeOH (8 mL). The reaction mixture was placed on a hydrogenation shaker and subjected to hydrogenation under a pressure of 65 psi for 18 h. The reaction mixture was filtered through Celite and washed with copious amounts solvent of MeOH/CH$_2$Cl$_2$ (80/20, v/v). The filtrate was collected and concentrated under reduced pressure and the resulting residue was purified with silica gel chromatography (CHCl$_3$:MeOH=10:1, R$_f$=0.36) to afford 1c (24 mg, 93%) as a white powder. $[\alpha]_D^{25}$+35° (c=0.5, pyridine). $^1$H NMR (600 MHz, C$_5$D$_5$N) δ 0.88 (t, J=6.6 Hz, 6H), 1.27-1.39 (m, 52H), 1.68-1.72 (m, 4H), 2.43-2.49 (m, 4H), 3.95 (dd, J=10.2, 6.0 Hz, 1H), 4.30 (dd, J=10.2, 6.0 Hz, 1H), 4.47-4.51 (m, 3H), 4.55-4.58 (m, 2H), 4.67 (d, J=2.4 Hz, 1H), 4.72 (dd, J=9.6, 3.6 Hz, 1H), 4.77 (dd, J=11.4, 3.6 Hz, 1H), 5.44 (d, J=3.6 Hz, 1H), 5.70 (m, 1H). $^{13}$C NMR (150 MHz, C$_5$D$_5$N) δ 14.7, 23.4, 25.7, 29.8, 30.0, 30.1, 30.2, 30.3, 30.4, 30.5, 32.6, 34.7, 34.9, 63.0, 63.4, 66.7, 70.8, 71.2, 71.4, 71.9, 73.6, 101.7, 173.6, 173.8. ESIMS calc'd for C$_{43}$H$_{82}$NaO$_{10}$ [M+Na]$^+$ 781.58. found: 781.32.

Example 2

Preparation of Compound 1b

This example provides a method for preparing compound 1b by reaction of an α-iodo galactopyranose with compound 7. Compound 7 is prepared as described below (see also scheme in FIG. 1).

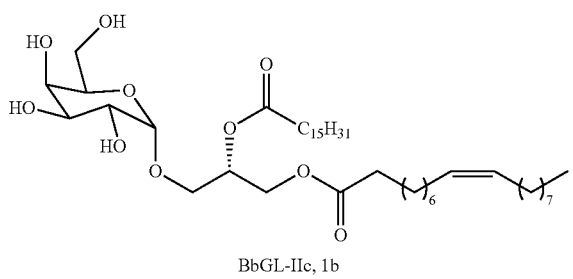

BbGL-IIc, 1b

3-O-Benzyl-sn-glycerol

To a solution of S(+) 2,2-dimethyl-1,3-dioxolane-4-methanol (0.48 g, 3.63 mmol) in DMF (5 mL) at 0° C. was added NaH (0.13 g, 5.45 mmol) portion wise, followed by benzyl bromide (0.68 g, 3.99 mmol). The reaction was allowed to reach rt and stirred overnight. It was quenched with addition of a few drops of methanol followed by ethyl acetate (10 mL) and water (10 mL). The organic layer was separated and the aqueous layer was extracted with ethyl acetate (3×10 mL). Combined organic layer was dried on anhyd. sodium sulfate and concentrated in vacuo to get crude residue as a colorless oil. $^1$H NMR (600 MHz, CDCl$_3$), δ 1.36 (s, 3H, CH$_3$), 1.41 (s, 3H, CH$_3$), 3.46 (dd, J=5.4, 10.4 Hz, 1H, CH$_2$), 3.55 (dd, J=5.4, 10.4 Hz, 1H, CH$_2$), 3.73 (dd, J=8.4, 6.6 Hz, 1H, CH$_2$), 4.05 (dd, J=8.4, 6.6 Hz, 1H, CH$_2$), 4.30 (dt, J=6.0, 12.0 Hz, 1H, CH), 4.55, 4.59 (AB q, J=12.0 Hz, 2H, PhCH$_2$), 7.20-7.40 (m, 5H, ArH); $^{13}$C NMR (150 MHz, CDCl$_3$) δ 25.6, 27.0, 67.1, 71.3, 73.8, 75.0, 109.6, 127.87, 127.96, 127.98, 128.0, 128.6, 138.2.

This crude product was added with 70% aqueous AcOH solution (10 mL). The reaction mixture was heated at 80° C. for 30 min and concentrated in vacuo. Flash column chromatography (EtOAc; hexane 1:1 (Rf=0.3)) afforded pure diol (0.52 g, 79% in 2 steps). IR (CHCl$_3$) cm$^{-1}$ 3366, 2896, 1496, 1453, 1365, 1209, 1073, 741, 698 cm$^{-1}$; $^1$H NMR (300 MHz, CDCl$_3$) δ 2.78 (brs, 2H, OH), 3.46 (dd, J=6.6, 9.6 Hz, 1H, CH$_2$OBn), 3.55 (dd, J=5.4, 9.6 Hz, 1H, CH$_2$OBn), 3.60 (dd, J=6.0, 12.0 Hz, 1H, CH$_2$OH), 3.68 (dd, J=3.6, 12.0 Hz, 1H, CH$_2$OH), 3.88 (tt, J=2.1, 3.9 Hz, 1H, CH), 4.58 (s, 2H, PhCH$_2$), 7.20-7.40 (m, 5H, ArH); $^{13}$C NMR (150 MHz, CDCl$_3$) δ 64.0, 70.7, 71.7, 73.5, 127.8, 127.9, 128.5, 137.6.

3-O-Benzyl-1-O-oleyl-sn-glycerol

A solution of 3-O-benzyl-sn-glycerol (400 mg, 2.20 mmol) in dry CH$_2$Cl$_2$ (12 mL) was cooled to 0° C. An 8 mL solution of DCC (906 mg, 4.39 mmol), DMAP (10 mg, 0.07 mmol) and oleic acid (620 mg, 2.19 mmol) in CH$_2$Cl$_2$ was added to it in a slow drop-wise manner over a period of 1 h. The reaction was stirred for 12 h at rt. The mixture was filtered over Celite, washed with saturated aqueous sodium bicarbonate solution and brine, dried on anhyd. sodium sulfate and concentrated in vacuo. The residue was purified by flash column chromatography using silica gel (hexane:EtOAc=4:1, R$_f$=0.35) to get monoacylated product (568 mg, 58%) as colorless oil. [α]$_D^{28}$+1° (C=1.1, CHCl$_3$); IR (CHCl$_3$) cm$^{-1}$ 3448, 3004, 2923, 2854, 1734, 1656, 1456, 1369, 1253, 1175, 1096, 1021, 735, 697 cm$^{-1}$; $^1$H NMR (600 MHz, CDCl$_3$) δ 0.88 (t, J=7.2 Hz, 3H, CH$_3$), 1.24-1.36 (m, 20H, CH$_2$), 1.60 (dt, J=7.2, 14.4 Hz, 2H, CH$_2$), 2.02 (dd, J=6.6, 13.2 Hz, 4H, CH$_2$), 2.31 (t, J=7.8 Hz, 2H, CH$_2$), 2.60 (s, 1H, OH), 3.46 (dd, J=6.0, 9.0 Hz, 1H, CH$_2$OBn), 3.55 (dd, J=4.8, 9.6 Hz, 1H, CH$_2$OBn), 4.00-4.06 (m, 1H, CHOH), 4.13 (dd, J=6.6, 11.4 Hz, 1H, CH$_2$OAcyl), 4.18 (dd, J=4.2, 11.4 Hz, 1H, CH$_2$OAcyl), 4.58 (s, 1H, PhCH$_2$), 5.35 (ddd, J=6.0, 11.4, 15.6 Hz, 2H, CH=CH), 7.20-7.40 (m, 5H, ArH); $^{13}$C NMR (150 MHz, CDCl$_3$) δ 14.1, 22.6, 24.9, 27.1, 27.2, 29.0, 29.1, 29.3, 29.5, 29.6, 29.7, 31.9, 34.1, 65.3, 68.9, 70.8, 73.5, 127.7, 127.8, 128.4, 129.7, 130.0, 137.6, 173.9; EMSI calc'd for C$_{28}$H$_{46}$NaO$_4$ [M+Na]$^+$ 469.33. found: 469.50.

3-O-Benzyl-1-O-oleyl-2-O-palmitoyl-sn-glycerol

A 4 mL solution of DCC (111 mg, 0.54 mmol), DMAP (3 mg, 0.02 mmol) and palmitic acid (86 mg, 0.34 mmol) in CH$_2$Cl$_2$ was cooled to 0° C. A solution of 3-O-benzyl-1-O-oleyl-sn-glycerol (100 mg, 0.228 mmol) in CH$_2$Cl$_2$ (2 mL) was added to it in a drop-wise manner and stirred for 12 h at rt. The mixture was filtered over Celite, washed with saturated aqueous sodium bicarbonate solution and brine, dried on anhydrous sodium sulfate and concentrated in vacuo. The residue was purified by flash column chromatography using silica gel (hexane:EtOAc=15:1, R$_f$=0.35) to get the product (154 mg, quantitative) as colorless oil. [α]$_D^{28}$+5° (c=2.0, CHCl$_3$); IR (CHCl$_3$) cm$^{-1}$ 2924, 2854, 1742, 1651, 1460, 1369, 1241, 1164, 1109, 1028, 733, 698 cm$^{-1}$; $^1$H NMR (600 MHz, CDCl$_3$) δ 0.88 (t, J=7.2 Hz, 6H, CH$_3$), 1.22-1.38 (m, 44H, CH$_2$), 1.52 (dt, J=7.2, 14.4 Hz, 4H, CH$_2$), 1.94 (dd, J=6.6, 12.6 Hz, 4H, CH$_2$), 2.20 (t, J=7.8 Hz, 2H, CH$_2$), 2.24 (t, J=7.8 Hz, 2H, CH$_2$), 3.51 (ddd, J=5.0, 10.2, 15.6 Hz, 2H, CH$_2$OBn), 4.11 (dd, J=5.4, 12.0 Hz, 1H, CH$_2$OAcyl), 4.27 (dd, J=3.6, 12.0 Hz, 1H, CH$_2$OAcyl), 4.44, 4.48 (ABq, J=12.0 Hz, 2H, PhCH$_2$), 4.06 (dt, J=4.2, 9.0 Hz, 1H, CH), 5.35 (ddd, J=6.0, 11.4, 15.6 Hz, 2H, CH=CH), 7.20-7.32 (m, 5H, ArH); $^{13}$C NMR (150 MHz, CDCl$_3$) δ 14.1, 22.65, 22.66, 24.8, 24.9, 27.1, 27.2, 29.06, 29.09, 29.16, 29.27, 29.29, 29.33, 29.46, 29.50, 29.61, 29.63, 29.67, 29.74, 31.88, 31.90, 34.1, 34.3, 62.6, 68.2, 70.0, 73.3, 127.6, 127.7, 128.4, 129.7, 130.0, 137.7, 173.0, 173.3; EMSI calc'd for C$_{44}$H$_{76}$NaO$_5$ [M+Na]$^+$ 707.56. found: 707.50.

1-O-Oleyl-2-O-palmitoyl-sn-glycerol 7

To a solution of 3-O-benzyl-1-O-oleyl-2-O-palmitoyl-sn-glycerol (110 mg, 0.16 mmol) in 2 mL CH$_2$Cl$_2$ at −78° C., boron trichloride (0.35 mL, 0.35 mmol) (1 M in CH$_2$Cl$_2$) was added over a period of 15 min. The reaction was stirred for 30 min under argon. The contents of the flask were then poured over ice water, the aqueous layer separated and extracted with CH$_2$Cl$_2$ (10 mL×3), dried over anhydrous sodium sulfate and concentrated in vacuo. The crude product was purified using silica gel column chromatography (hexane:EtOAc=19:1~7:1 (R$_f$=0.35) gradient) to get the alcohol (66 mg, 69%) as colorless oil. [α]$_D^{27}$ −3° (C=1.1, CHCl$_3$); IR (CHCl$_3$) cm$^{-1}$ 3442, 2911, 2853, 1736, 1652, 1460, 1374, 1239, 1167, 1116, 1094, 1053, 722, 700 cm$^{-1}$; $^1$H NMR (600 MHz, CDCl$_3$) δ 0.88 (t, J=7.2 Hz, 6H, CH$_3$), 1.22-1.36 (m, 44H, CH$_2$), 1.52 (dt, J=7.2, 14.4 Hz, 4H, CH$_2$), 1.94 (dd, J=6.0, 12.0 Hz, 4H, CH$_2$), 2.05 (s, 1H, OH), 2.20 (t, J=7.8 Hz, 2H, CH$_2$), 2.24 (t, J=7.8 Hz, 2H, CH$_2$), 3.72 (s, 2H, CH$_2$OH), 4.25 (dd, J=6.0, 12.0 Hz, 1H, CH$_2$OAcyl), 4.31 (dd, J=4.8, 12.0 Hz, 1H, CH$_2$OAcyl), 4.00-4.06 (dt, J=4.8, 10.2 Hz, 1H, CH), 5.35 (ddd, J=6.0, 10.8, 16.2 Hz, 2H, CH=CH); $^{13}$C NMR (150 MHz, CDCl$_3$) δ 14.1, 22.66, 22.67, 24.78, 24.82, 24.84, 24.91, 27.14, 27.19, 29.06, 29.08, 29.15, 29.25, 29.30, 29.46, 29.50, 29.60, 29.63, 29.66, 29.67, 29.71, 29.74, 31.83, 31.88, 31.90, 34.1, 34.3, 61.5, 62.0, 72.1, 129.7, 130.0, 173.4, 173.8; EMSI calc'd for $C_{37}H_{70}NaO_5$ [M+Na]$^+$ 617.51. found: 617.60.

1-O-Oleoyl-2-O-Palmitoyl-3-O-α-D-galactopyranosyl-sn-glycerol (BbGL-II, 1b)

To a solution of 1,2,3,4,6-penta-O-trimethylsilyl-D-galactopyranose (4, 55 mg, 0.10 mmol) in CH$_2$Cl$_2$ (1.5 mL) at 0° C. was added TMSI (22 mg, 0.11 mmol). The reaction was stirred under argon at 0° C. for 20 min. The reaction was stopped by adding 15 mL of anhydrous benzene and solvent was evaporated under reduced pressure. The slightly yellow oil 5 was dissolved in CH$_2$Cl$_2$ (1.5 mL) and kept under argon. In a separate flask, molecular sieves (MS, 4 Å, 50 mg), TBAI (114 mg, 0.30 mmol), 7 (20 mg, 0.034 mmol) and DIPEA (39 mg, 0.30 mmol) were added into CH$_2$Cl$_2$ (1.5 mL). The mixture was stirred under argon at rt. 2,3,4, 6-tetra-trimethylsilylgalactopyranosyl iodide was added dropwise and the reaction mixture was stirred at rt for 36 h. Solvent was evaporated. MeOH (15 mL) and Dowex® 50WX8-200 ion exchange resin (0.5 g) were added and the reaction was stirred at rt for 4 h. Resin was removed by filtration. The solvent was removed in vacuo and the resulting residue was purified by silica gel chromatography (CHCl$_3$:MeOH=10:1, R$_f$=0.36) to afford 1b as a white powder (18 mg, 72%). [α]$_D^{27}$+46° (c=1.1, CHCl$_3$); IR (CHCl$_3$) cm$^{-1}$ 3458, 3397, 2915, 2852, 1734, 1656, 1462, 1378, 1242, 1150, 1073, 1054, 971, 799, 720 cm$^{-1}$; $^1$H NMR (600 MHz, CDCl$_3$) δ 0.87 (t, J=6.9 Hz, 6H, CH$_3$), 1.24-1.36 (m, 44H, CH$_2$), 1.59 (dd, J=6.9, 13.5 Hz, 4H, CH$_2$), 2.00 (dd, J=6.0, 12.0 Hz, 4H, CH$_2$), 2.31 (dt, J=4.2, 5.4 Hz, 4H, CH$_2$), 2.80 (s, 2H, OH), 3.55 (s, 1H, OH), 3.61 (dd, J=10.8, 6.0 Hz, 1H, H-3a), 3.74-3.94 (m, 6H, H-2', H-4', H-5', H-6a', H-6b', H-3b), 4.03-4.12 (m, 1H, H-3'), 4.13 (dd, J=6.0, 12.0 Hz, 1H, H-1a), 4.36 (dd, J=2.4, 12.0 Hz, 1H, H-1b), 4.92 (d, J=2.4 Hz, 1H, H-1'), 5.24 (dt, 1H, J=5.4, 10.2 Hz, H-2), 5.34 (ddd, J=6.0, 11.4, 20.4 Hz, 2H, CH=CH); $^{13}$C NMR (150 MHz, CDCl$_3$) δ 14.1, 22.68, 22.69, 24.85, 24.90, 27.17, 27.21, 29.11, 29.13, 29.15, 29.21, 29.31, 29.36, 29.5, 29.66, 29.69, 29.71, 29.76, 31.90, 31.92, 34.1, 34.3, 62.2, 62.8, 66.6, 69.2, 69.8, 70.0, 70.2, 70.7, 99.3, 129.7, 130.0, 173.3, 173.6; HRMS MALDI calc'd for $C_{43}H_{80}NaO_{10}$ [M+Na]$^+$ 779.5614. found: 779.5434.

Example 3

Preparation of Compound 2

This example provides a method for preparing compound 2 by reaction of an α-iodo galactopyranose with compound 8. Compound 8 is prepared as described below.

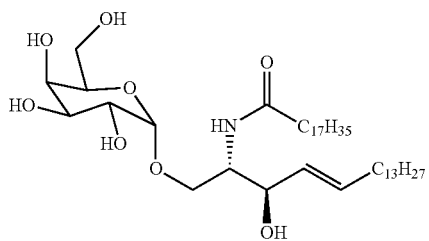

2

(2S,3R,4E)-2-(N-stearoylamino)-4-octadecene-1,3-diol (8)

To a solution of sphingosine (100 mg, 0.33 mmol) in CH$_2$Cl$_2$ (3 mL) was added EDCI (128 mg, 0.66 mmol) and DMAP (cat.). Under stirring, stearic acid (95 mg, 0.33 mmol in 10 mL CH$_2$Cl$_2$) was added dropwise over a period time of 16 h. The reaction was stirred under argon for 24 h at rt. Solvent was evaporated and the residue was applied to silica gel column chromatography (CHCl$_3$:MeOH=9:1, R$_f$=0.43) to afford 8 as a white powder (140 mg, 75%). $^1$H NMR (600 MHz, CDCl$_3$) δ 0.88 (t, J=6.8 Hz, 6H), 1.26-1.40 (m, 50H), 1.64 (t, J=7.2 Hz, 2H), 2.06 (dd, J=14.4, 7.2 Hz, 2H), 2.24 (t, J=7.2 Hz, 2H), 3.71 (m, 1H), 3.91-3.97 (m, 2H), 4.32 (m, 1H), 5.42 (dd, J=15.6, 6.6 Hz, 1H), 5.79 (dt, J=15.6, 6.6 Hz, 1H), 6.28 (d, J=7.2 Hz, 1H). $^{13}$C NMR (150 MHz, CDCl$_3$) δ 14.3, 22.9, 26.0, 29.4, 29.5, 29.6, 29.7, 29.8, 29.9, 32.2, 32.6, 54.7, 62.8, 74.9, 129.0, 134.6, 174.2. ESIMS calc'd for $C_{36}H_{71}NNaO_3$ [M+Na]$^+$ 588.53. found: 588.18.

(2S,3R,4E)-1-O-(α-D-Galactopyranosyl)-2-(N-octadecanosylamino)-4-1,3-octadecenediol (2)

To a solution of 1,2,3,4,6-penta-O-trimethylsilyl-D-galactopyranose (4, 108 mg, 0.20 mmol) in CH$_2$Cl$_2$ (3 mL) at 0° C. was added TMSI (40 mg, 0.20 mmol). The reaction was stirred under argon for 15 min. and was stopped by adding 15 mL of anhydrous benzene. Solvent was evaporated under reduced pressure and the slightly yellow oil (5) was dissolved in CH$_2$Cl$_2$ (10 mL) and kept under argon. In a separate flask, molecular sieves (MS, 4 Å, 50 mg), TBAI (220 mg, 0.60 mmol), 8 (38 mg, 0.066 mmol) and DIPEA (77 mg, 0.60 mmol) were added into CH$_2$Cl$_2$ (1.5 mL). The mixture was stirred under argon at rt. The glycosyl iodide 5 was added dropwise and the reaction mixture was stirred at rt for 48 h. Solvent was evaporated. MeOH (15 mL) and Dowex® 50WX8-200 ion exchange resin (1 g) were added and the reaction was stirred at rt for 4 h. Resin was removed by filtration. The solvent was removed in vacuo and the resulting residue was purified by silica gel chromatography (CHCl$_3$:MeOH=87:13, R$_f$=0.35). The slightly yellow powder was washed with small amount of cold EtOAc (1 mL) to afford 2 as a white powder (37 mg, 77%). [α]$_D^{25}$+29° (c=1.0, CHCl$_3$). $^1$H NMR (600 MHz, CDCl$_3$/CD$_3$OD=9:1) δ 0.82 (t, J=7.2 Hz, 6H), 1.20-1.35 (m, 50H), 1.54 (t, J=7.8 Hz, 2H), 1.98 (dd, J=14.4, 7.2 Hz, 2H), 2.13 (t, J=7.2 Hz, 2H), 3.61 (dd, J=10.8, 4.8 Hz, 1H), 3.66-3.78 (m, 6H), 3.91-3.93 (m, 2H), 4.03 (d, J=6 Hz, 1H), 4.81 (d, J=3.6 Hz, 1H), 5.38 (dd, J=15.6, 6.6 Hz, 1H), 5.74 (dt, J=15.6, 6.6 Hz, 1H), 6.98 (d, J=9.0 Hz, 1H). $^{13}$C NMR (150 MHz, CDCl$_3$/CD$_3$OD=9:1) δ 14.2, 22.8, 26.0, 29.4, 29.5, 29.6, 29.7, 29.8, 29.9, 32.1, 32.5, 36.7, 53.6, 62.2, 68.1, 69.1, 70.0, 70.4, 70.5, 72.9, 100.0, 128.9, 134.2, 174.7. ESIMS calc'd for $C_{42}H_{81}NNaO_8$ [M+Na]$^+$ 750.59. found: 750.66.

Example 4

Preparation of Compound 3

This example provides a method for preparing compound 3 by reaction of an α-iodo galactopyranose with compound 9. Compound 9 is prepared as described below. Compound 3 can also be prepared via microwave, as described below.

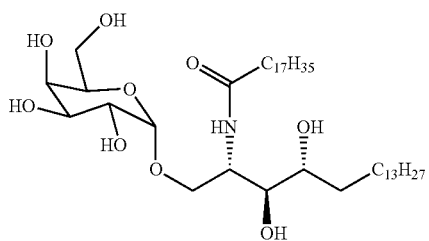

(2S,3R,4R)-2-(N-stearoylamino)-octadecane-1,3,4-triol (9)

To a solution of phytosphingosine (99 mg, 0.31 mmol) in pyridine (3 mL) was added EDCI (128 mg, 0.66 mmol) and DMAP (cat.). Under stirring, stearic acid (90 mg, 0.31 mmol, in 15 mL $CH_2Cl_2$) was added dropwise over a period time of 16 h. The reaction was stirred under argon for 24 h at rt. Solvent was evaporated and the residue was applied to silica gel column chromatography ($CHCl_3$:MeOH=88:12, $R_f$=0.35) to afford 9 as a white powder (120 mg, 68%). $^1$H NMR (600 MHz, $CDCl_3$:$CD_3OD$=90:10) δ 0.74 (t, J=7.2 Hz, 6H), 1.11-1.64 (m, 52), 1.31-1.58 (m, 4H), 2.07 (d, J=7.8 Hz, 2H), 3.40 (m, 2H), 3.55 (dd, J=11.4, 5.4 Hz, 1H), 3.64 (dd, J=11.4, 3.6 Hz, 2H). $^{13}$C NMR (150 MHz, $CDCl_3$:$CD_3OD$=90:10) δ 13.9, 22.6, 25.8, 25.9, 29.3, 29.4, 29.5, 29.6, 29.7, 29.8, 29.9, 31.9, 33.1, 36.6, 52.1, 61.2, 72.6, 75.8, 174.7. ESIMS calc'd for $C_{36}H_{73}NNaO_4$ $[M+Na]^+$ 606.54. found: 606.54.

(2S,3S,4R)-1-O-(α-D-Galactopyranosyl)-2-(N-octadecanosylamino)-1,3,4-octadecanetriol (3)

The synthetic protocol of 3 is the same as described for compound 2 as a white powder (15 mg, 30%). $^1$H NMR (600 MHz, $C_5D_5N$) δ 0.88 (t, J=6.8 Hz, 6H), 1.25-1.34, m, 50H), 1.68 (m, 1H), 1.82 (m, 2H), 1.88 (m, 2H), 2.35 (m, 1H), 2.46 (t, J=7.2 Hz, 2H), 4.35 (m, 2H), 4.40-4.48 (m, 4H), 4.53-4.58 (m, 2H), 4.65-4.70 (m, 2H), 5.30 (m, 1H), 5.61 (d, J=3.6 Hz, 1H), 8.54 (d, J=9.2 Hz, 1H). $^{13}$C NMR (150 MHz, $C_5D_5N$) δ 14.6, 23.3, 26.7, 26.9, 30.0, 30.1, 30.2, 30.23, 30.3, 30.4, 30.5, 30.7, 32.5, 34.7, 37.2, 51.9, 63.1, 69.1, 70.7, 71.4, 71.9, 72.9, 73.4, 77.1, 101.9, 173.6. ESIMS calc'd for $C_{42}H_{83}NO_9$ $[M+Na]^+$ 768.60. found: 768.78.

Microwave-Assisted Glycosylation and One-Pot Synthesis of Compound 3

To a solution of 1,2,3,4,6-penta-O-trimethylsilyl-D-galactopyranose (4, 33 mg, 0.051 mmol) in $CH_2Cl_2$ (3 mL) at 0° C. was added TMSI (12.4 mg, 0.051 mmol). The reaction was stirred at 0° C. for 20 min and was stopped by adding 15 mL of anhydrous benzene. Solvent was removed under reduced pressure and the slightly yellow oil 5 was dissolved in $CH_2Cl_2$ (3 mL) and was transferred into a 10 mL microwave reaction test tube. TBAI (19 mg, 0.051 mmol), 9 (30 mg, 0.051 mmol) and DIPEA (20 mg, 0.153 mmol) were added into the test tube and the tube was placed into a microwave reactor. The reaction was conducted at 130° C. for 90 min at 225 watts. The reaction mixture was transferred to a flask and solvent was removed under reduced pressure. MeOH (10 mL) and Dowex® 50WX8-200 ion exchange resin (1 g) was added and the reaction was stirred at rt for 4 h. The work-up and purification was the same as mentioned above to afford 3 as white powder (37 mg, 67%).

TABLE 2

Microwave results.

| Entry | Donor | solvent | Reaction Condition | Yield (%) | α/β ratio |
|---|---|---|---|---|---|
| 1 | 3 eq. | benzene | 80° C., 1.5 h, 25 Watts | 20 | α only |
| 2 | 3 eq. | $CH_2Cl_2$ | 80° C., 1.5 h, 30 Watts | 30 | α only |
| 3 | 1 eq. | $CH_2Cl_2$ | 100° C., 1.5 h, 35 Watts | 30 | α only |
| 4 | 1 eq. | $CH_2Cl_2$ | 120° C., 1.5 h, 37 Watts | 37 | α only |
| 5 | 1 eq. | $CH_2Cl_2$ | 120° C., 1.5 h, 225 Watts | 67 | α only |

Example 5

Preparation of Compound 14

This example provides a method for preparing compound 14 by reaction of an α-iodo glucopyranose with n-octanol.

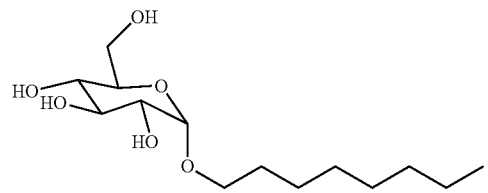

Octyl α-D-glucopyranoside (14)

To a solution of 1,2,3,4,6-penta-O-trimethylsilyl-D-glucopyranose (13, 715 mg, 1.32 mmol) in $CH_2Cl_2$ (3 mL) at 0° C. was added TMSI (194 mg, 0.97 mmol). The reaction was stirred under argon for 45 min. In a separate flask, molecular sieves (MS, 4 Å, 50 mg), TBAI (975 mg, 2.64 mmol), n-octanol (115 mg, 0.88 mmol) and DIPEA (341 mg, 2.64 mmol) were added into $CH_2Cl_2$ (1.5 mL). The mixture was stirred under argon at rt. The glycosyl iodide was added dropwise and the reaction mixture was stirred at rt for 48 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography ($CHCl_3$:MeOH=9:1, $R_f$=0.23 to afford 14 as a white powder (209 mg, 81%). $^1$H NMR (600 MHz, $CDCl_3$) δ 0.86 (t, J=7.2 Hz, 3H), 1.22-1.30 (m, 10H), 1.58 (p, J=6.6 Hz, 2H), 3.40-3.44 (m, 1H), 3.52-3.63 (m, 4H), 3.72 (d, J=8.4 Hz, 2H), 3.87 (d, J=10.8 Hz, 1H), 4.82 (d, J=2.4 Hz, 1H). $^{13}$C NMR (150 MHz, $CDCl_3$) δ 14.3, 22.9, 26.3, 29.5, 29.7, 29.7, 32.1, 61.3, 68.7, 69.5, 71.7, 72.1, 74.4, 98.8. ESIMS calc'd for $C_{14}H_{28}NaO_6$ $[M+Na]^+$ 315.18. found: 315.72.

Example 6

Preparation of Compound 15

This example provides a method for preparing compound 15 by reaction of an α-iodo glucopyranose with compound 6.

23

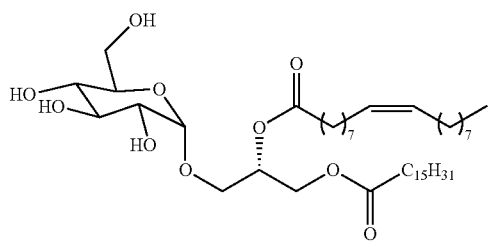

1-O-Palmitoyl-2-O-oleoyl-3-O-α-D-glucopyranosyl-sn-glycerol (15)

To a solution of 1,2,3,4,6-penta-O-trimethylsilyl-D-glucopyranose (13, 136 mg, 0.25 mmol) in CH$_2$Cl$_2$ (3 mL) at 0° C. was added TMSI (56 mg, 0.28 mmol). The reaction was stirred under argon at 0° C. for 20 min. In a separate flask, molecular sieves (MS, 4 Å, 50 mg), TBAI (186 mg, 0.50 mmol), 6 (50 mg, 0.08 mmol) and DIPEA (65 mg, 0.50 mmol) were added into CH$_2$Cl$_2$ (1.5 mL). The mixture was stirred under argon at rt. The glycosyl iodide was added dropwise and the reaction mixture was stirred at rt for 24 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography (CHCl$_3$:MeOH=10:1, R$_f$=0.36) to afford 15 as a white powder (36 mg, 58%). $^1$H NMR (600 MHz, CDCl$_3$) δ 0.88 (t, J=6.6 Hz, 7H), 1.25-1.30 (m, 44H), 1.60 (bs, 4H), 2.00 (dd, J=12.0, 6.0 Hz, 4H), 2.31 (dd, J=11.4, 7.2, Hz, 4H), 3.51 (s, 1H), 3.56 (m, 1H), 3.61 (m, 3H), 3.73 (bt, 1H), 3.82 (bs, 3H), 4.15 (dd, J=11.4, 6.0 Hz, 1H), 4.39 (d, J=9.6 Hz, 1H), 4.86 (bs, 1H), 5.25 (bt, 1H), 5.34 (dt, J=15.6, 6.8 Hz, 2H). $^{13}$C NMR (150 MHz, CDCl$_3$) δ 14.3, 22.83, 22.85, 25.0, 27.35, 27.38, 29.12, 29.19, 29.28, 29.31, 29.32, 29.35, 29.49, 29.52, 29.63, 29.65, 29.66, 29.69, 29.74, 32.06, 32.08, 34.3, 34.4, 61.7, 62.7, 66.3, 69.9, 72.0, 72.2, 74.3, 99.3, 129.8, 130.2, 173.5, 173.9. ESIMS calc'd for C$_{43}$H$_{80}$NaO$_{10}$ [M+Na]$^+$ 779.56. found: 779.43.

Example 7

Preparation of Compound 16

This example provides a method for preparing compound 16 by reaction of an α-iodo glucopyranose with compound 8.

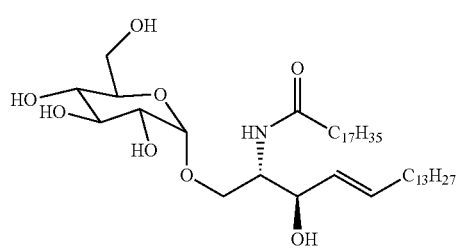

24

(2S,3R,4E)-1-O-(α-D-Glucopyranosyl)-2-(N-octadecanosylamino)-4-1,3-octadecenediol (16)

To a solution of 1,2,3,4,6-penta-O-trimethylsilyl-D-glucopyranose (13, 162 mg, 0.30 mmol) in CH$_2$Cl$_2$ (3 mL) at 0° C. was added TMSI (66 mg, 0.33 mmol). The reaction was stirred under argon for 15 min. In a separate flask, molecular sieves (MS, 4 Å, 50 mg), TBAI (222 mg, 0.60 mmol), 8 (56 mg, 0.10 mmol) and DIPEA (77 mg, 0.60 mmol) were added into CH$_2$Cl$_2$ (1.5 mL). The mixture was stirred under argon at rt. The glycosyl iodide was added dropwise and the reaction mixture was stirred at rt for 48 h. Solvent was evaporated. MeOH (15 mL) and Dowex® 50WX8-200 ion exchange resin (1 g) were added and the reaction was stirred at rt for 4 h. The resin was removed by filtration. The solvent was removed in vacuo and the resulting residue was purified by silica gel chromatography (CHCl$_3$:MeOH=87:13, R$_f$=0.35) to afford 16 as a white powder (45 mg, 63%). $^1$H NMR (600 MHz, CDCl$_3$/CD$_3$OD=9:1) δ 0.69 (t, J=7.2 Hz, 6H), 1.07-1.11 (m, 50H), 1.16-1.18 (m, 2H), 1.40-1.41 (m, 2H), 1.84 (q, J=7.2 Hz, 2H), 2.00 (t, J=7.2 Hz, 2H), 3.19 (t, J=9.6 Hz, 1H), 3.26 (dd, J=9.6, 4.2 Hz, 1H), 3.36 (dt, J=4.2, 3.3 Hz, 1H), 3.471 (t, J=9 Hz, 1H), 3.53 (dd, J=6.0, 1.2 Hz, 1H), 3.55 (t, J=3.0 Hz, 1H), 3.59 (t, J=4.2 Hz, 1H), 3.61 (t, J=3.0 Hz, 1H), 3.77 (p, J=3.6 Hz, 1H), 3.91 (t, J=6.6 Hz, 1H), 4.63 (d, J=3.6 Hz, 1H), 5.26 (dd, J=14.4, 6.6 Hz, 1H), 5.54 (dt, J=13.8, 6.6 Hz, 1H). $^{13}$C NMR (150 MHz, CDCl$_3$/CD$_3$OD=9:1) δ 13.7, 22.5, 25.8, 29.0, 29.1, 29.1, 29.2, 29.3, 29.4, 31.7, 32.2, 36.3, 53.4, 61.3, 67.2, 70.0, 71.9, 71.9, 73.6, 73.9, 99.3, 128.9, 134.21 174.5. ESIMS calc'd for C$_{42}$H$_{81}$NNaO$_8$ [M+Na]$^+$ 750.59. found: 750.6.

Example 8

Preparation of Compound 17

This example provides a method for preparing compound 17 by reaction of an α-iodo lactopyranose with n-octanol.

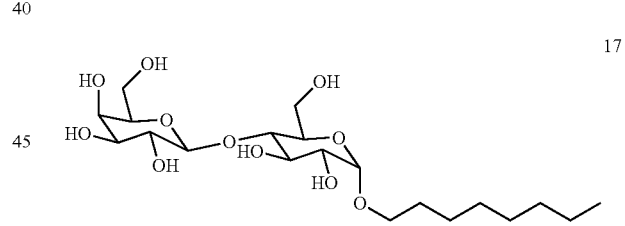

Reaction with TBAI Catalyst

Octyl α-D-lactopyranoside (17)

To a solution of per-O-trimethylsilyl-D-lactopyranose (12, 210 mg, 0.23 mmol) in CH$_2$Cl$_2$ (2 mL) at 0° C. was added TMSI (45 mg, 0.23 mmol). The reaction was stirred under argon at 0° C. for 30 min. In a separate flask, molecular sieves (MS, 3 Å, 100 mg), TBAI (252 mg, 0.69 mmol), octanol (20 mg, 0.15 mmol) and DIPEA (89 mg, 0.68 mmol) were added into CH$_2$Cl$_2$ (1.5 mL). The mixture was stirred under argon at rt. The glycosyl iodide was added dropwise and the reaction mixture was stirred at rt for 16 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography (CHCl$_3$:MeOH=5:5, R$_f$=0.49) to afford 17 as a white powder (24 mg, 35%). The spectra are in complete agreement with those previously reported in the literature.

Reaction with NIS Catalyst

Octyl α-D-lactopyranoside (17)

To a solution of per-O-trimethylsilyl-D-lactopyranose (12, 230 mg, 0.25 mmol) in CH$_2$Cl$_2$ (2 mL) at 0° C. was added TMSI (50 mg, 0.25 mmol). The reaction was stirred under argon at 0° C. for 30 min. In a separate flask, N-iodosuccinimide (62 mg, 0.28 mmol), octanol (11 mg, 0.08 mmol) and DIPEA (97 mg, 0.75 mmol) were added into CH$_3$CN (2 mL). The mixture was stirred under argon at rt. The glycosyl iodide was added dropwise and the reaction mixture was stirred at rt for 24 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography (CHCl$_3$:MeOH=7:3, R$_f$=0.25) to afford 17 as a white powder (22 mg, 58%). The spectra are in complete agreement with those previously reported in the literature.

Example 9

Preparation of Compound 10

Figure 2:
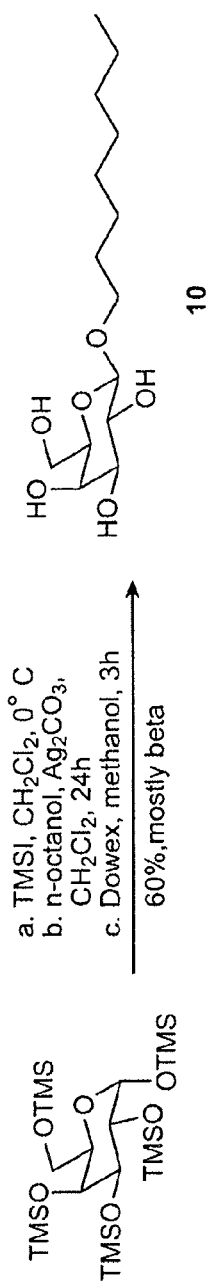
FIG. 2 shows the synthesis of octyl β-D-glucopyranoside (10).

This example provides a method for preparing compound 10 by reaction of an α-iodo glucopyranose with n-octanol (see also scheme in FIG. 2).

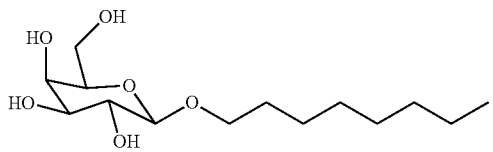

Octyl β-D-glucopyranoside (10)

To a solution of 1,2,3,4,6-penta-O-trimethylsilyl-D-glucopyranose (13, 105 mg, 0.19 mmol) in CH$_2$Cl$_2$ (1.5 mL) at 0° C. was added TMSI (38.8 mg, 0.19 mmol). The reaction was stirred under argon for 30 min. In a separate flask, Ag$_2$CO$_3$ (71.2 mg, 0.26 mmol), n-octanol (8.4 mg, 0.06 mmol) and DIPEA (75.2 mg, 0.58 mmol) were added into CH$_2$Cl$_2$ (1.5 mL). The mixture was stirred under argon at rt. The glycosyl iodide was added dropwise and the reaction mixture was stirred at rt for 24 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography (CHCl$_3$:MeOH=9:1, R$_f$=0.23 to afford 10 as a white powder (11.3 mg, 60%). All spectra obtained were identical to those reported in the literature.

Example 10

Preparation of GalCer

Figure 3:
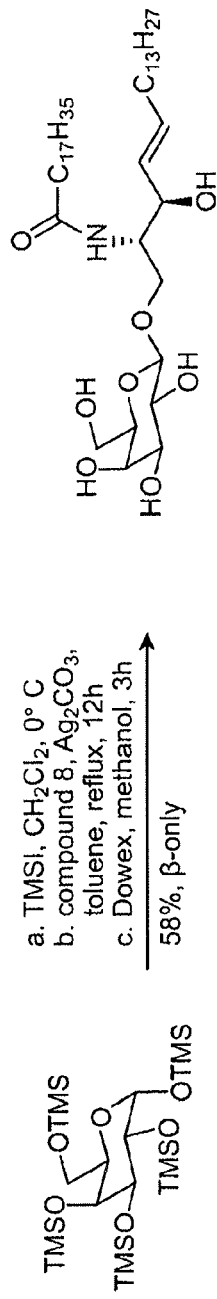
FIG. 3 shows the synthesis of (2S,3R,4E)-1-O-(β-D-Galactopyranosyl)-2-(N-octadecanosylamino)-4-1,3-octadecenediol (GalCer).

This example provides a method for preparing beta-GalCer by reaction of an α-iodo glucopyranose with compound 8 (see also scheme in FIG. 3).

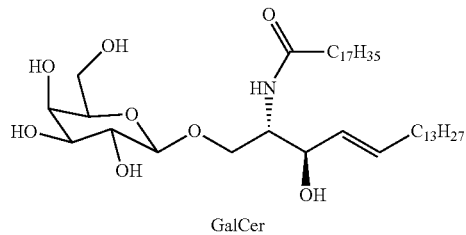

GalCer (2S,3R,4E)-1-O-(β-D-Galactopyranosyl)-2-(N-octadecanosylamino)-4-1,3-octadecenediol (GalCer)

To a solution of 1,2,3,4,6-penta-O-trimethylsilyl-D-glucopyranose (13, 57 mg, 0.11 mmol) in CH$_2$Cl$_2$ (1.5 mL) at 0° C. was added TMSI (0.21 mg, 0.11 mmol). The reaction was stirred under argon for 30 min. In a separate flask molecular sieves (MS, 4 Å, 100 mg), Ag$_2$CO$_3$ (58 mg, 0.21 mmol), 8 (40 mg, 0.07 mmol), and DIPEA (75.2 mg, 0.58 mmol) were added into toluene (1.5 mL). The mixture was stirred under argon at reflux conditions of 110° C. The glycosyl iodide was added dropwise and the reaction mixture was stirred at 110° C. for 48 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography to afford beta-GalCer as a white powder (58%, β-only, 1:1 mixture of mono and diglycosylated products). All spectra obtained were identical to those reported in the literature.

Example 11

Preparation of Compound BbGL1

Figure 4:
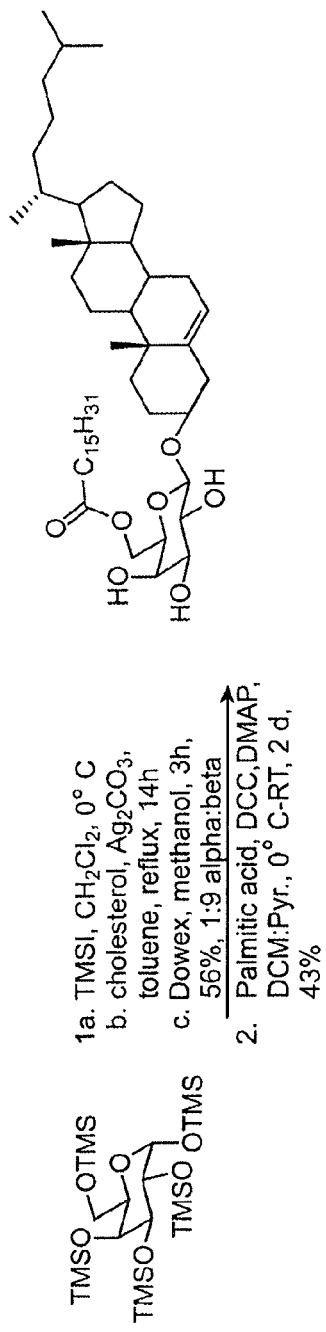
FIG. 4 shows the synthesis of cholesteryl 6-O-acyl-β-D-galactopyranoside (BbGL1).

This example provides a method for preparing compound BbGL1 by reaction of an α-iodo galactopyranose with cholesterol (see also scheme in FIG. 4).

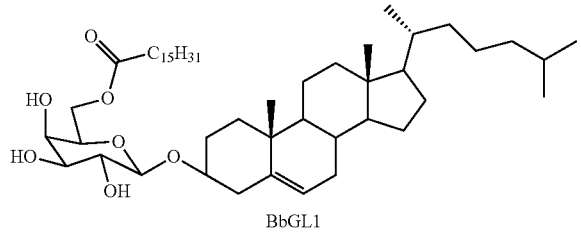

BbGL1

Cholesteryl 6-O-acyl(3D-galactopyranoside (BbGL1)

To a solution of 1,2,3,4,6-penta-O-trimethylsilyl-D-glucopyranose (13, 200 mg, 0.37 mmol) in CH$_2$Cl$_2$ (1.5 mL) at 0° C. was added TMSI (74 mg, 0.37 mmol). The reaction was stirred under argon for 25 min. In a separate flask molecular sieves (MS, 4 Å, 200 mg), Ag$_2$CO$_3$ (204 mg, 0.74 mmol), cholesterol (50 mg, 0.13 mmol), and DIPEA (75.2 mg, 0.58 mmol) were added into toluene (4 mL). The mixture was stirred under argon and refluxing at 110° C. The glycosyl iodide was added dropwise and the reaction mixture was stirred at rt for 14 h. Solvent was evaporated. MeOH (15 mL) and Dowex® 50WX8-200 ion exchange resin (1 g) were added and the reaction was stirred at rt for 4 h. The resin was removed by filtration. The solvent was removed in vacuo and the resulting residue was purified by silica gel chromatography to afford BbGL1 as a white powder (39 mg, 56%, mostly β). All spectra obtained were identical to those reported in the literature. A solution of the beta-cholesteryl-glycoside (130 mg, 0.24 mmol) in dry pyridine (4 mL) was cooled to 0° C. A 2 mL solution of DCC (98 mg, 0.48 mmol), DMAP (15 mg, 0.105 mmol) and palmitic acid (92 mg, 0.36 mmol) in CH$_2$Cl$_2$ was added to it in a slow drop-wise manner over a period of 1 h. The reaction was stirred for 48 h at rt. The mixture was filtered over celite, washed with saturated aqueous sodium bicarbonate solution and brine, dried on anhyd. sodium sulfate and concentrated in vacuo. The residue was purified by flash column chromatography using silica gel (methanol:CH$_2$Cl$_2$=4:1, R$_f$=0.35) to obtain monoacylated product (83 mg, 45%) as a colorless oil. All spectra obtained were identical to those reported in the literature.

TABLE 1

One-pot Synthesis and Optimization of BbGL1

| Entry | Temp | Solvent | Time | Yield | α/β ratio |
|---|---|---|---|---|---|
| 1 | RT | DCM | 4 d | 50% | 1/1 |
| 2 | 110 | Toluene | 14 h | 55% | 1/6 |
| 3 | 110 | Toluene | 3 h | 38% | 1/6 |
| 4 | 110 | Toluene | 4 h | 46% | 1/5.5 |
| 5 | 110 | Toluene | 3 h | 43% | 1/4.5-5 |
| 6 | RT | CH$_3$CN:DCM | 50 h | 35% | 1.6/1 |
| 7 | 110 | Toluene slower addition | 24 h | 56% | 1/9 |

Example 12

Preparation of Compound 11

Figure 5:
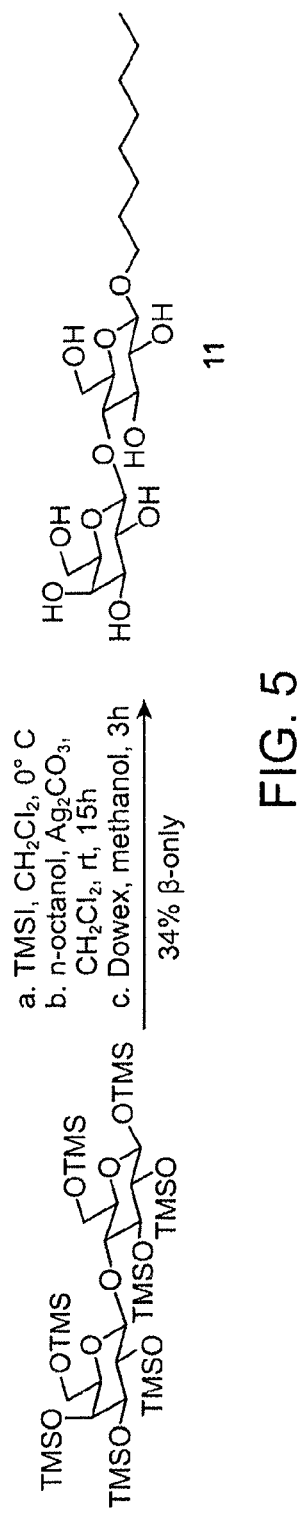
FIG. 5 shows the synthesis of octyl β-D-lactopyranoside (11).

This example provides a method for preparing compound 11 by reaction of an α-iodo lactopyranose with n-octanol (see also scheme in FIG. 5).

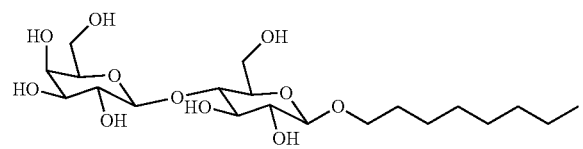

Octyl β-D-lactopyranoside (11)

To a solution of per-O-trimethylsilyl-D-lactopyranose (12, 220 mg, 0.24 mmol) in CH$_2$Cl$_2$ (2 mL) at 0° C. was added TMSI (50.2 mg, 0.24 mmol). The reaction was stirred under argon for 25 min. In a separate flask, Ag$_2$CO$_3$ (88.2 mg, 0.32 mmol), n-octanol (10.4 mg, 0.08 mmol) and DIPEA (93.1 mg, 0.72 mmol) were added into CH$_2$Cl$_2$ (2 mL) and the mixture was stirred under argon at rt. The glycosyl iodide was added dropwise and the reaction mixture was stirred for 15 h. Solvent was evaporated. MeOH (15 mL) and Dowex® 50WX8-200 ion exchange resin (1 g) were added and the reaction was stirred at rt for 3 h. The resin was removed by filtration. The solvent was removed in vacuo and the resulting residue was purified by silica gel chromatography (CHCl$_3$:MeOH=7:3, R$_f$=0.23) to afford 11 as a white powder (12.3 mg, 34%). All spectra obtained were identical to those reported in the literature.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of preparing an unprotected β-O-glycolipid comprising the steps of:
   contacting a protected α-iodo sugar with a catalyst and a lipid comprising a hydroxy group, under conditions sufficient to prepare a protected β-O-glycolipid, wherein the protected α-iodo sugar is selected from the group consisting of:

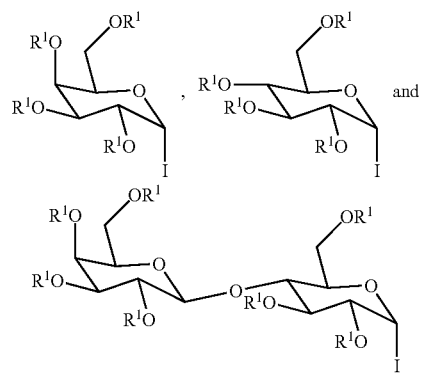

wherein
   each R$^1$ is independently selected from the group consisting of a trialkylsilyl and a protected saccharide selected from the group consisting of a monosaccharide, a disaccharide, a trisaccharide, an oligosaccharide and a polysaccharide, wherein the protected saccharide is protected with a trialkylsilyl,
   the catalyst is selected from the group consisting of silver halide, mercury cyanide, magnesium oxide and silver carbonate, and
   the lipid is a ceramide; and
   deprotecting the protected β-O-glycolipid under conditions sufficient to prepare the unprotected β-O-glycolipid, wherein the contacting and deprotecting steps are performed in a single vessel.

2. The method of claim 1, wherein the trialkylsilyl is selected from the group consisting of trimethylsilyl, triethylsilyl, triisopropylsilyl and tert-butyl-dimethylsilyl.

3. The method of claim 1, wherein the catalyst is silver carbonate.

4. The method of claim 1, wherein the method of preparing an unprotected β-O-glycolipid is performed using microwave irradiation.

* * * * *